US012011307B2

(12) United States Patent
Okuno (10) Patent No.: US 12,011,307 B2
(45) Date of Patent: Jun. 18, 2024

(54) X-RAY IMAGING DEVICE (71) Applicant: Shimadzu Corporation, Kyoto (JP)

(72) Inventor: Tomoharu Okuno, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 462 days.

(21) Appl. No.: 17/287,053

(22) PCT Filed: Oct. 30, 2018

(86) PCT No.: PCT/JP2018/040383
§ 371 (c)(1),
(2) Date: Apr. 20, 2021

(87) PCT Pub. No.: WO2020/090012
PCT Pub. Date: May 7, 2020

(65) Prior Publication Data
US 2021/0378613 A1 Dec. 9, 2021

(51) Int. Cl.
A61B 6/00 (2024.01)
A61B 6/46 (2024.01)

(52) U.S. Cl.
CPC .......... A61B 6/46 (2013.01); A61B 6/54 (2013.01); A61B 6/48 (2013.01)

(58) Field of Classification Search
CPC .......... A61B 6/46; A61B 6/48; A61B 6/54
See application file for complete search history.

(56) References Cited

U.S. PATENT DOCUMENTS

2008/0183475 A1 7/2008 Hirota et al.
2016/0166222 A1* 6/2016 Kim .................... A61B 6/0492
378/37

FOREIGN PATENT DOCUMENTS

| JP | 1-141647 A | 6/1989 |
| JP | 4-59894 B2 | 9/1992 |
| JP | 2000-325339 A | 11/2000 |
| JP | 2008-67935 A | 3/2008 |

OTHER PUBLICATIONS

First Japanese Office Action dated Sep. 28, 2021 for corresponding Japanese Patent Application No. 2020-554651, submitted with a machine translation.

(Continued)

Primary Examiner — Mark R Gaworecki
(74) Attorney, Agent, or Firm — Muir Patent Law, PLLC (57) ABSTRACT When a first-stage push-button switch of an operation unit (2) is pressed, an X-ray imaging control unit (72) transmits a signal A for starting voice guidance to a signal output unit (73) for a voice guidance unit as well as a signal B for starting preparation of X-ray imaging to an X-ray tube control unit (71). At this time, when the pushing operation of the push-button switch is performed, the X-ray imaging control unit (72) immediately transmits the signal A for starting the voice guidance to the signal output unit (73) for the voice guidance unit but transmits the signal B for starting the X-ray imaging after a time t1 has elapsed. The time t1 is a time calculated by subtracting a time t3 required for preparing an X-ray tube (42) for performing X-ray imaging from a time t2 required for the voice guidance.

6 Claims, 6 Drawing Sheets (56) References Cited

OTHER PUBLICATIONS

Second Office Action dated Apr. 5, 2022 for corresponding Japanese Application No. JP 2020-554651, submitted with a machine translation.
Written Opinion by the International Search Authority for PCT application No. PCT/JP2018/040383 dated Oct. 22, 2019, submitted with a machine translation.
"RADspeed Pro Edge package" available at: https://www.shimadzu.com/med/products/radio/m-od0gjn00000025sa.html, downloaded on Feb. 17, 2021, this or similar version published at least as of Jun. 5, 2018.
"Voice Generator Nice Call" available at: http://www.san-kyo.co.jp/products/%E3%83%8A%E3%82%A4%E3%82%B9%E3%82%B3%E3%83%BC%E3%83%AB/, downloaded on Feb. 17, 2021, this or similar version published at least as of Jun. 5, 2018.
"Medical Voice" available at: http://www.orrad.co.jp/product_medicalvoice.php, downloaded on Feb. 17, 2021, this or similar version published at least as of Jun. 5, 2018.
Notice of Allowance dated Aug. 30, 2022 for corresponding Japanese Patent Application No. JP 2020-554651.

* cited by examiner

X-RAY IMAGING DEVICE

TECHNICAL FIELD

The present invention relates to an X-ray imaging apparatus, and more particularly to an X-ray imaging apparatus having a voice guidance function.

BACKGROUND ART

In a diagnostic X-ray imaging apparatus for diagnosing a respiratory system of a subject, it is required to make the timing of respiration of the subject coincide with the timing of the X-ray imaging. For example, in a case of chest radiography in which X-ray imaging is performed with the lungs inflated, it is required that the subject hold the breath with largely inhaled and X-ray imaging be performed by emitting X-rays during the breath-holding. If the lungs move due to respiration during the X-ray irradiation, the captured X-ray image may be blurred, affecting the diagnosis.

For this reason, it has been proposed to output voice guidance at the time of X-ray imaging (see Patent Document 1 and Patent Document 2). A voice guidance device called "AutoVoice" is on sale to support a subject for the breath-holding timing. When this voice guidance device is used, the announcement of "Inhale and hold the breath" is issued from the voice guidance device to the subject at the timing when the X-ray preparation start switch of the X-ray imaging apparatus is pressed, in conjunction with the X-ray imaging operation by the X-ray imaging apparatus. When the X-ray imaging switch of the X-ray imaging apparatus is subsequently pressed, X-rays are emitted from the X-ray imaging apparatus. After completion of this X-ray imaging, an X-ray image is acquired. Upon completion of this X-ray imaging, an announcement of "X-ray imaging has been completed" is issued from the voice guidance device.

In addition to general imaging in which a single X-ray image is captured by performing X-ray irradiation only once when the X-ray imaging switch is pressed, serial imaging (serial radiography) may sometimes be performed in which a plurality of X-ray images is sequentially captured during which the X-ray imaging switch is kept pressed. At the time of this serial imaging, for example, in a case where the frame rate is 15 fps (frames per second), X-ray imaging is performed 225 times in 15 seconds.

In this voice guidance at the time of the serial imaging, for example, an announcement for urging the subject to inhale air is issued from the voice guidance device for five (5) seconds after the first pressing of the preparation button of the X-ray imaging in the X-ray imaging apparatus. Next, an announcement is made by the voice guidance device for instructing the subject to hold his/her breath for two (2) seconds from when the X-ray imaging switch of the X-ray imaging apparatus is pressed to when the X-ray imaging is initiated. While continuously performing successive X-ray imaging, the voice guidance device issues an announcement to prompt the subject to exhale during the next five (5) seconds, and the voice guidance device subsequently makes an announcement to instruct the subject to hold the breath for two (2) seconds, and then the voice guidance device makes an announcement prompt the subject to exhale during the next five (5) seconds. Then, the pressing of the X-ray imaging switch in the X-ray imaging apparatus is released, and in two (2) second, an announcement indicating that the imaging has been completed is made by the voice guidance device.

PRIOR ART DOCUMENT

Patent Document

Patent Document 1: Japanese Unexamined Patent Application Publication No. 2000-325339
Patent Document 2: Japanese Unexamined Patent Application Publication No. 2008-67935

SUMMARY OF THE INVENTION

Problems to be Solved by the Invention

Conventionally, voice guidance by a voice guidance device is started when the imaging preparation button, which is an operation unit button for causing the imaging unit to start preparation of X-ray imaging, is pressed, and a certain time is required from the start of the voice guidance to the end thereof. In particular, at the time of serial imaging, since a subject needs to perform a plurality of operations in succession, the time of the voice guidance until first X-ray imaging is started will also be longer.

Since the preparation (ready up) operation of the X-ray imaging in the imaging unit has started with the voice guidance, in a case where the voice guidance time becomes longer, the preparation operation of the imaging unit will also be performed for a long time. The preparation operation of X-ray imaging in an imaging unit includes, for example, the heating operation of the filament in the X-ray tube and the rotation operation of the rotating anode in the X-ray tube. When the preparation operation of the imaging unit is executed for a long time, the filament is continuously heated for a long time. Therefore, a load is applied to the filament, resulting in the reduced life of the filament. Alternatively, the rotating anode continuously rotates for a long time, causing unnecessary abrasion of the bearing or the like in the rotation holding unit, which shortens the life of the bearing or the like.

The present invention has been made to solve the above-described problems, and an object thereof is to provide an X-ray imaging apparatus capable of further reducing the preparation time of X-ray imaging in an imaging unit.

Means for Solving the Problem

According to the invention as recited in claim 1, an X-ray imaging apparatus includes:
  an imaging unit configured to perform X-ray imaging of a subject, the imaging unit being provided with an X-ray tube and an X-ray detector;
  a voice guidance unit configured to output voice guidance to the subject;
  an operation unit configured to cause the imaging unit to start preparation of the X-ray imaging; and
  a control unit configured to cause the voice guidance unit to start the voice guidance when the operation unit is operated and cause the X-ray tube to start preparation of X-ray irradiation after a time t1 has elapsed since an operation of the operation unit.

According to the invention as recited in claim 2, in the invention recited in claim 1, the control unit sets the time t1 based on a time required for the voice guidance.

According to the invention as recited in claim 3, in the invention recited in claim 2, when a time required for the voice guidance is t2 and a time from when the X-ray tube starts the preparation of the X-ray irradiation until when the X-ray irradiation is enabled is t3, the control unit determines the time t1 by the following expression: t1=t2−t3.

According to the invention as recited in claim 4, in the invention recited in any one of claims 1 to 3, it is selectable whether to set the time t1 or whether to set the time t1 to zero.

According to the invention as recited in claim 5, in the invention recited in claim 4, it is selectable whether or not to use the voice guidance unit, and the control unit sets the time t1 to zero when the voice guidance unit is not used.

According to the invention as recited in claim 6, in the invention recited in claim 5, the control unit determines whether or not to use the voice guidance unit based on an anatomical program at the time of the X-ray imaging.

Effects of the Invention

According to the invention as recited in claim 1, since the X-ray tube is caused to start preparation of the X-ray irradiation after the time t1 has elapsed since the voice guidance is started in accordance with the operation of the operation unit, it is possible to make the preparation time of the X-ray imaging in the imaging unit shorter. Therefore, it is possible to prevent the shortening of the life of the X-ray tube in the imaging unit.

According to the invention as recited in claim 2, it is possible to shorten the preparation time of the X-ray imaging in the imaging unit corresponding to the time required for the voice guidance.

According to the invention as recited in claim 3, it is possible to make the end time of the voice guidance coincide with the preparation completion time of the X-ray irradiation.

According to the invention as recited in claim 4, it is possible to select whether or not to delay the preparation start time of the X-ray irradiation.

According to the invention as recited in claim 5, it is possible to delay the preparation start time of the X-ray irradiation only when using the voice guidance unit.

According to the invention as recited in claim 6, it is possible to determine whether or not to use the voice guidance based on an anatomical program.

EMBODIMENTS FOR CARRYING OUT THE INVENTION

Figure 1:
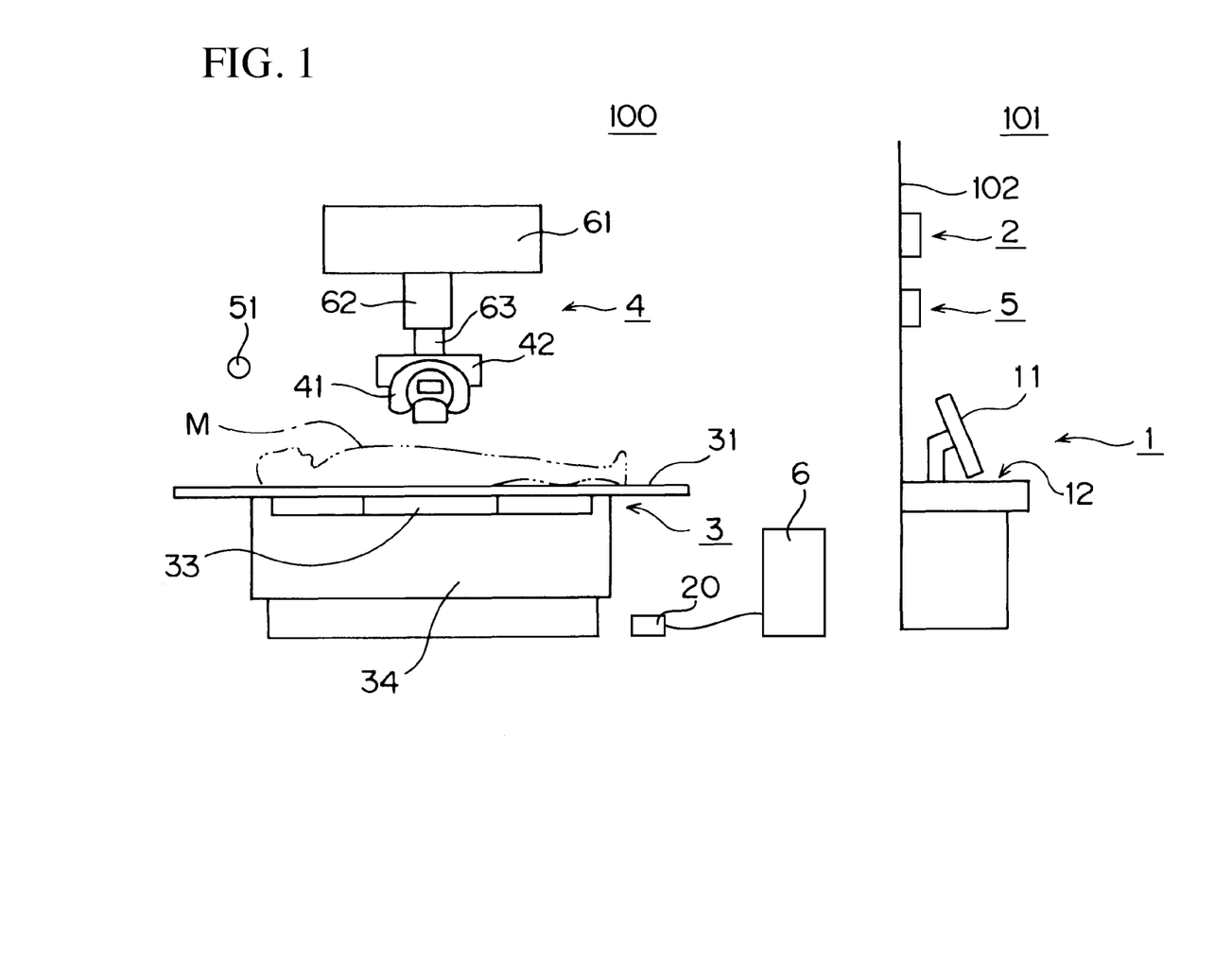
FIG. 1 is a schematic diagram of an X-ray imaging apparatus according to the present invention.
Figure 2:
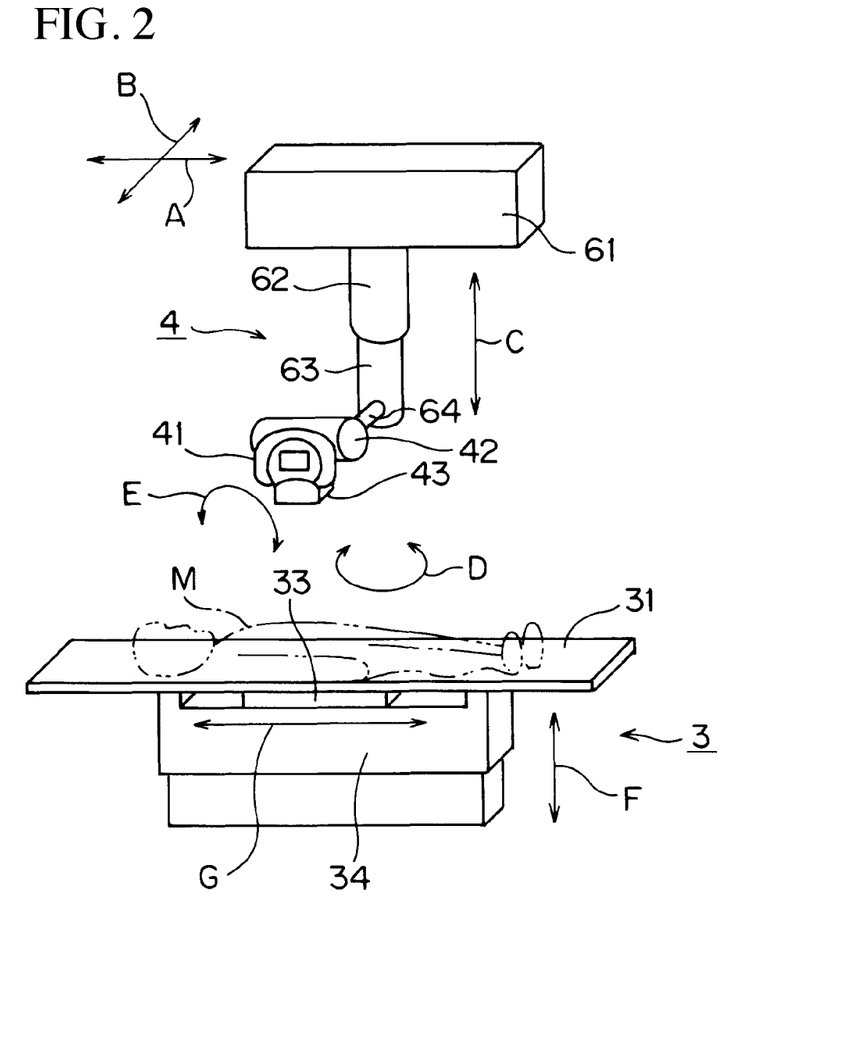
FIG. 2 is a perspective view of an examination table 3 and an imaging unit 4 in the X-ray imaging apparatus according to the present invention.

Hereinafter, some embodiments of the present invention will be described with reference to the attached drawings. FIG. 1 is a schematic diagram of an X-ray imaging apparatus according to the present invention. FIG. 2 is a perspective view of an examination table 3 and an imaging unit 4 in an X-ray imaging apparatus according to the present invention.

The X-ray imaging apparatus according to the present invention is provided with a console unit 1, an operation unit 2, a voice guidance unit 5, an examination table 3, and an imaging unit 4. The console unit 1, the operation unit 2, and the voice guidance unit 5 are installed in an operation room 101 for an operator to perform X-ray imaging operations, etc. The examination table 3 and the imaging unit 4 are installed in an imaging room 100 for imaging a subject M. The imaging room 100 and the operation room 101 are shielded by a partition wall 102.

The console unit 1 installed in the operation room 101 is provided with a display unit 11 composed of a liquid crystal display and the like and an operation unit 12 composed of a keyboard, a mouse, and the like for performing various operations. X-ray images and the like are displayed on the display unit 11. The console unit 1 is connected to an in-hospital network, which is an in-hospital communication of a subject control system in a hospital (not shown).

The voice guidance unit 5 provided in the operation room 101 is constituted by a commercially available voice guidance device called an "Auto Voice". The voice guidance unit 5 is for generating voice guidance for supporting the breath-holding timing of the subject M and is connected to a speaker 51 disposed on a wall or the like of the imaging room 100.

Figure 3:
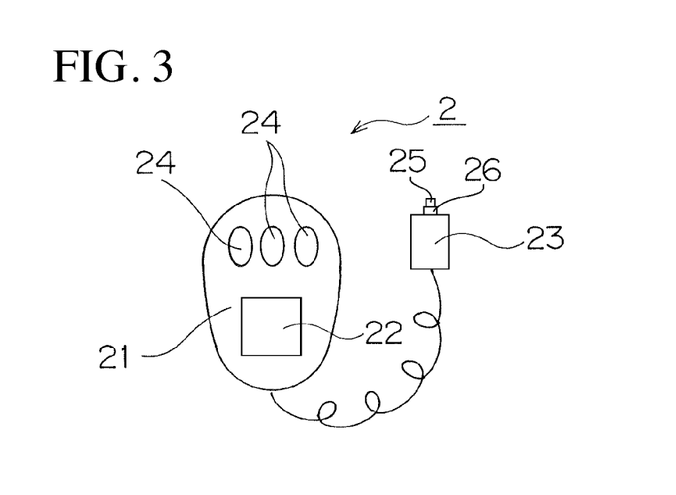
FIG. 3 is a schematic diagram of an operation unit 2.

FIG. 3 is a schematic diagram of the operation unit 2.

The operation unit 2 is provided on the partition wall 102 in the operation room 101. The operation unit 2 is provided with a control panel 21 including a touch panel type liquid crystal display unit 22 and input buttons 24 and a hand switch 23 having two-stage push-button switches 25 and 26 for transmitting a signal for X-ray irradiation or the preparation for the X-ray tube 42 in the imaging unit 4. The push-button switch 25 is for causing the X-ray tube 42 in the imaging unit 4 to start preparation of the X-ray imaging. Further, the push-button switch 26 is for starting X-ray imaging by irradiating X-rays from the X-ray tube 42. This operation unit 2 is used to set X-ray irradiation condition of a tube voltage or a tube current of the X-ray tube 42 or an X-ray irradiation time. This operation unit 2 is connected to the high-voltage generation unit 6 provided in the imaging room 100 shown in FIG. 1. This high-voltage generation unit 6 provides a high voltage to the X-ray tube 42 to allow irradiation of X-rays. Note that the high-voltage generation unit 6 is connected to a foot switch 20 used to start irradiation of X-rays in the imaging room 100.

The examination table 3 shown in FIG. 1 and FIG. 2 is provided with a top board 31 for placing a subject M thereon, an X-ray detection unit 33 in which a flat panel detector (FPD) as an X-ray detector is housed, and a raising and lowering unit 34 for raising and lowering the top board 31 and the X-ray detection unit 33. The X-ray detection unit 33 is horizontally movable in the G-direction shown in FIG. 2. Further, the X-ray detection unit 33 can be moved upward and downward together with the top board 31 in the F-direction as shown in FIG. 2.

As shown in FIG. 2, the imaging unit 4 is provided with a base unit 61 movable in the A-direction and the B-direction perpendicular to each other with respect to the ceiling of the imaging room 100, a support portion 62 extending downward from the base unit 61, a moving portion 63 movable in the C-direction with respect to the support portion 62 and rotatable in the D-direction, and a support shaft 64 pivotably attached to the lower end portion of the moving portion 63 and configured to integrally rotate the handle 41, the X-ray tube 42, and the collimator 43 in the E-direction. Therefore, the handle 41, the X-ray tube 42, and the collimator 43 are movable in the A-direction, the B-direction, the C-direction, the D-direction, and the E-direction.

Figure 4:
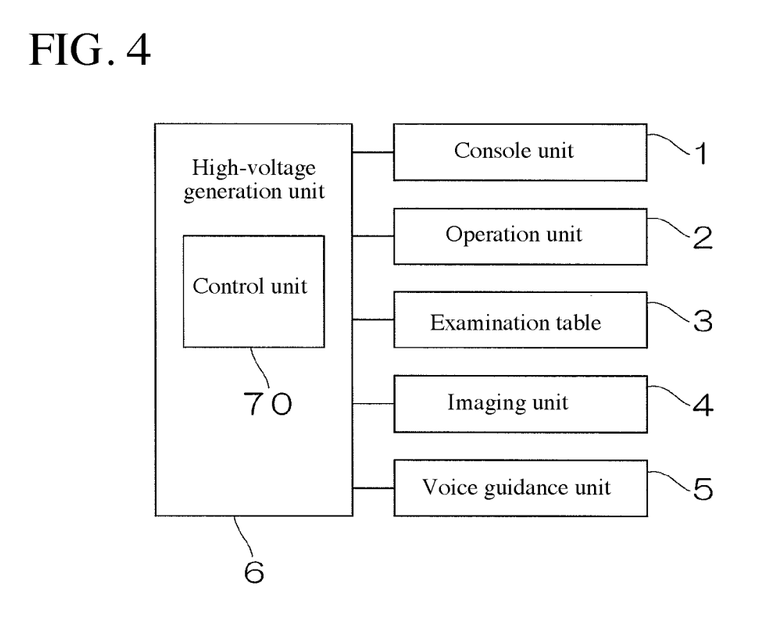
FIG. 4 is a block diagram showing a main control system of the X-ray imaging apparatus.

FIG. 4 is a block diagram showing the main control system of the X-ray imaging apparatus according to the present invention.

The high-voltage generation unit 6 is provided with a control unit 70 for controlling the entire device. The control unit 70 is configured by a computer with software installed. The various features included in the control unit 70 are realized by executing the software installed on the computer. The control unit 70 in the high-voltage generation unit 6 is connected to the console unit 1, the operation unit 2, the examination table 3, the imaging unit 4, and the voice guidance unit 5.

Note that, in the embodiment shown in FIG. 4, an example is shown in which the high-voltage generation unit 6 is provided with the control unit 70. However, this control unit 70 may be disposed in, for example, a member other than the high-voltage generation unit 6, such as, e.g., the console unit 1. Alternatively, the function of the control unit 70 may be disposed in a plurality of members in a divided manner. In the embodiment shown in FIG. 4, the console unit 1, the operation unit 2, the examination table 3, the imaging unit 4, and the voice guidance unit 5 are connected to each other via the high-voltage generation unit 6, but these components may be connected to each other in any manner.

This X-ray imaging apparatus is capable of performing general imaging for capturing a single radiation image and a serial imaging for consecutively capturing a plurality of radiation images, as the operation of the imaging mechanism composed of the console unit 1, the operation unit 2, the examination table 3, the imaging unit 4, and the high-voltage generation unit 6. Which of the general imaging and the serial imaging is executed can be selected from the operation unit 12 of the console unit 1 and the operation unit 2. Further, whether or not to use the voice guidance unit 5 in this X-ray imaging apparatus can be selected. That is, the voice guidance unit 5 is used when the subject M is required to perform breath-holding or the like when performing chest radiography or the like. On the other hand, the voice guidance unit 5 is not used when imaging a leg or the like. Whether or not to use the voice guidance unit 5 can be selected from the operation unit 12 of the console unit 1 or the operation unit 2. Note that whether or not to use the voice guidance unit 5 may be determined in association with an anatomical program selected at the time of the X-ray imaging.

Figure 5:
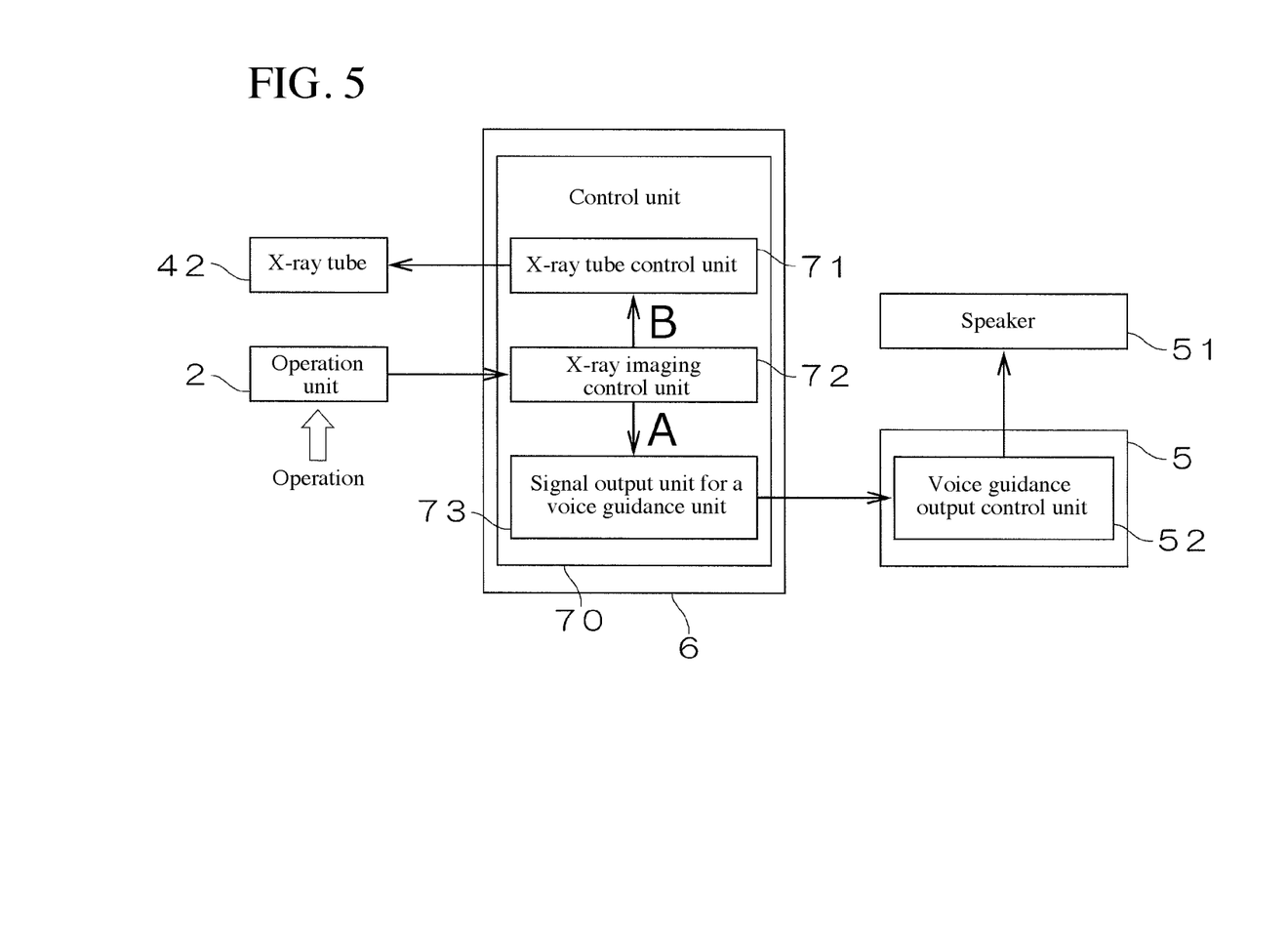
FIG. 5 is a block diagram showing a transmission state of a command signal when executing X-ray imaging using voice guidance according to a voice guidance unit 5.
Figure 6:
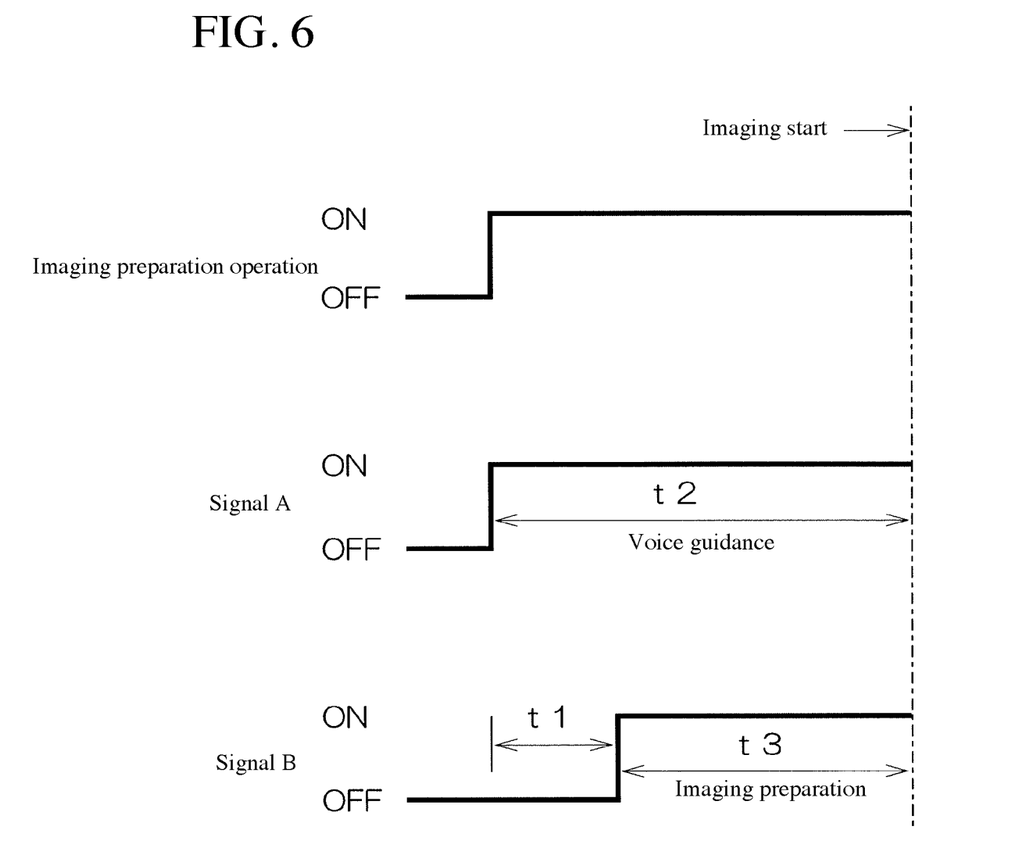
FIG. 6 is a time chart illustrating timings of an operation for starting the preparation of the X-ray imaging, a signal A for starting the voice guidance, and a signal B for starting the preparation of the X-ray imaging.

FIG. 5 is a block diagram showing a transmission state of a command signal when executing X-ray imaging using the voice guidance according to the voice guidance unit 5. Further, FIG. 6 is a time chart showing the timing of the operation for starting preparation of X-ray imaging, a signal A for starting the voice guidance, and a signal B for starting preparation of the X-ray imaging. Note that the horizontal axis in FIG. 6 shows the time. In FIG. 6, the time required for the voice guidance is denoted as t2, and the time required for the preparation of the X-ray tube 42 for performing X-ray imaging is denoted as t3.

When the operator presses the first-stage push-button switch 25 in the operation unit 2 to cause the imaging unit 4 to start preparation of the X-ray imaging at the start of the X-ray imaging, a signal is transmitted to the X-ray imaging control unit 72 in the control unit 70. The X-ray imaging control unit 72 transmits a signal A to start the voice guidance to the signal output unit 73 for a voice guidance unit. With this, a signal is transmitted from the signal output unit 73 for a voice guidance unit to the voice guidance output control unit 52 of the voice guidance unit 5, so that voice guidance is generated from the speaker 51. The type of the voice guidance is selected based on the anatomical program at the X-ray imaging. Note that the voice guidance may be set in advance. In parallel with this, the X-ray imaging control unit 72 transmits a signal B to cause the X-ray tube control unit 71 to start preparation of the X-ray imaging.

At this time, as shown in FIG. 6, when the pushing operation of the push-button switch 25 as the imaging preparation operation is executed, the X-ray imaging control unit 72 immediately transmits the signal A for starting the voice guidance to the signal output unit 73 for a voice guidance unit. In contrast, the X-ray imaging control unit 72 transmits a signal B for starting the preparation of X-ray imaging to the X-ray tube control unit 71 after the time t1 has elapsed. The time t1 is a time obtained by subtracting the time t3 required for the X-ray tube 42 to prepare the X-ray imaging from the time t2 required for the voice guidance, as shown in the following expression: t1=t2−t3.

As described above, since the X-ray tube 42 is caused to start the preparation operation after the time t1 has elapsed since the pressing of the push-button switch 25, as shown in FIG. 6, it is possible to make the end time of the voice guidance coincide with the end time of the imaging preparation. Then, at the time when the voice guidance and the imaging preparation have been completed, the operator presses the second stage of the push-button switch 26 to execute the X-ray imaging by irradiating X-rays from the X-ray tube 42.

With this, the X-ray imaging can be started immediately after the time required to prepare X-ray imaging has elapsed. Therefore, the preparation time of the X-ray tube 42 is minimized. With this, it is possible to prevent the phenomenon that the life of the X-ray tube 42 is shortened due to the fact that the filament is loaded by being continuously heated for a long time or that the bearing, etc., of the rotation holding unit of the rotating anode is unnecessarily worn by the continuous rotation of the rotating anode for a long time.

Note that in the above-described embodiment, the time t1 is set as a time obtained by subtracting the time t3 required for the X-ray tube 42 to prepare the X-ray imaging from the time t2 required for the voice guidance. At this time, since the time t3 required for the X-ray tube 42 to prepare X-ray imaging is generally constant, the time t1 is set based on the time t2 required for the voice guidance. Note that the time t1 may be set to be larger to some extent than the time obtained by subtracting the time t3 required for X-ray tube 42 to prepare X-ray imaging from the time t2 required for the voice guidance.

Further, in a case where the time t2 required for the voice guidance differs depending on the type of the voice guidance, the time t1 may be changed for each time t2, or the time t1 may be set in accordance with the longest time t2.

Note that it may be selected that the time t1 is zero. The time t1 is defined as a time after the pushing operation of the push-button switch 25 as an imaging preparation operation is executed until the signal B for making the X-ray tube control unit 71 start preparation of X-ray imaging is transmitted. For example, in a case where the voice guidance according to the voice guidance unit 5 is not used, the operator may set the time t1 to 0 by operating the console unit 1 or the operation unit 2.

At this time, when the operator selects an anatomical program for performing X-ray imaging by operating the console unit 1 or the operation unit 2, it may be determined whether or not to use voice guidance by the voice guidance unit 5 based on the anatomical program selected by the control unit 70.

DESCRIPTION OF SYMBOLS

1: Console unit
2: Operation unit
3: Examination table
4: Imaging unit
5: Voice guidance unit
6: High-voltage generation unit
11: Display unit
12: Operation unit
20: Foot switch
23: Hand switch
25: Push-button switch
26: Push-button switch
31: Top board
33: X-ray detection unit
41: Handle
42: X-ray tube
43: Collimator
51: Speaker
52: Voice guidance output control unit
70: Control unit
71: X-ray tube control unit
72: X-ray imaging control unit
73: Signal output unit for a voice guidance unit
100: Imaging room
101: Operation room
M: Subject

The invention claimed is:

1. An X-ray imaging apparatus comprising:
an imaging unit configured to capture an X-ray image of a subject, the imaging unit being provided with an X-ray tube and an X-ray detector;
a voice guidance unit configured to output voice guidance to the subject;
an operation unit configured to receive a first operation for causing the imaging unit to start preparation of the X-ray tube for capturing the X-ray image; and
a control unit configured to:
recognize that the first operation has been performed on the operation unit;
cause the voice guidance unit to start the voice guidance in response to recognizing that the first operation has been performed on the operation unit; and
cause the X-ray tube to start the preparation of the X-ray tube for capturing the X-ray image after a time t1 elapses from recognizing that the first operation has been performed on the operation unit.

2. The X-ray imaging apparatus as recited in claim 1,
wherein the control unit sets the time t1 based on a time required for the voice guidance.

3. The X-ray imaging apparatus as recited in claim 2,
wherein when a time required for the voice guidance is t2 and a time from when the X-ray tube starts the preparation of the X-ray tube until when X-ray irradiation is enabled is t3, the control unit determines the time t1 by the following expression:

$$t1=t2-t3.$$

4. The X-ray imaging apparatus as recited in claim 1,
wherein it is selectable whether to set the time t1 or whether to set the time t1 to zero.

5. The X-ray imaging apparatus as recited in claim 4,
wherein it is selectable whether or not to use the voice guidance unit, and
wherein the control unit sets the time t1 to zero when the voice guidance unit is not used.

6. The X-ray imaging apparatus as recited in claim 5,
wherein the control unit determines whether or not to use the voice guidance unit based on an anatomical program at the time of capturing the X-ray image.

* * * * *